United States Patent [19]

Clozel et al.

[11] Patent Number: 5,620,975
[45] Date of Patent: Apr. 15, 1997

[54] PHARMACEUTICAL COMPOSITION AND METHOD FOR THE CONTROL OF HYPERTENSION

[75] Inventors: Jean-Paul Clozel, St. Louis, France; Rita Müller, Basel, Switzerland; Wolfgang Osterrieder, Grenzach-Wyhlen, Germany

[73] Assignee: Hoffmann-La Roche Inc., Nutley, N.J.

[21] Appl. No.: 333,171

[22] Filed: Nov. 2, 1994

Related U.S. Application Data

[63] Continuation of Ser. No. 210,095, Mar. 17, 1994, abandoned, which is a continuation of Ser. No. 909,357, Jul. 6, 1992, abandoned.

[30] Foreign Application Priority Data

Jul. 23, 1991 [CH] Switzerland .................. 2191/91

[51] Int. Cl.⁶ .................. A61K 31/55; A61K 31/415
[52] U.S. Cl. .................. 514/221; 514/395
[58] Field of Search .................. 514/221, 395

[56] References Cited

U.S. PATENT DOCUMENTS

| 4,658,024 | 4/1987 | Attwood et al. |
| 4,808,605 | 2/1989 | Branca et al. |
| 4,859,665 | 8/1989 | Garthoff et al. |
| 4,871,731 | 10/1989 | Walker. |
| 4,983,598 | 1/1991 | Cavero et al. |
| 5,110,813 | 5/1992 | Grupp et al. |

FOREIGN PATENT DOCUMENTS

| 0224810 | 7/1980 | European Pat. Off. |
| 0094095 | 5/1983 | European Pat. Off. |
| 0268148 | 11/1987 | European Pat. Off. |
| 0272177 | 11/1987 | European Pat. Off. |

OTHER PUBLICATIONS

Clozel et al., Cardiovasc. Drug Rev. 9, 4–17 (1991).
Hypertension, 9, 178–187 (1987).
J.Cardiovasc.Pharmacol. 7, 588–591 (1985).
Arzneimittelforschung Bd. 40, Nr. 4, 417–421, 1990.

Primary Examiner—Kimberly Jordan
Assistant Examiner—M. Moezie
Attorney, Agent, or Firm—George W. Johnston; Ellen Ciambrone Coletti

[57] ABSTRACT

Pharmaceutical composition comprising a tetrahydronaphthalene derivative of the formula

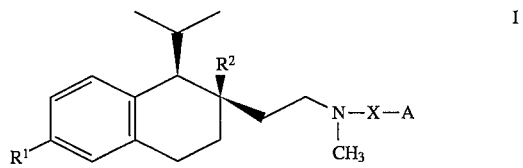

wherein $R^1$ is halogen, $R^2$ is lower-alkoxy-lower-alkyl-carbonyloxy, X is $C_2$–$C_8$-alkylene and A is benzimidazolyl optionally substituted at the N atom by alkyl with 1 to 12 C atoms,
and a pyridazodiazepine of the formula

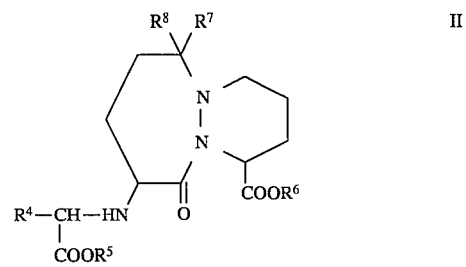

wherein $R^4$ is aralkyl with 1 to 6 C atoms in the alkyl residue and phenyl, which is optionally mono-substituted by halogen, alkoxy with 1 to 6 C atoms or phenyl, as the aryl residue, $R^5$ and $R^6$ each independently are hydrogen or alkyl with 1 to 6 C atoms and $R^7$ and $R^8$ each are hydrogen or together are an oxo group,
in the form of their free bases, their hydrates or their pharmaceutically usable salts for the simultaneous, separate or planned stepwise use in the control or prevention of circulatory disorders, especially hypertension.

2 Claims, 3 Drawing Sheets

PHARMACEUTICAL COMPOSITION AND METHOD FOR THE CONTROL OF HYPERTENSION

This is a continuation of application Ser. No. 08/210,095 filed Mar. 17, 1994, now abandoned which is a Rule 62 Continuation of Ser. No. 07/909,357, filed Jul. 6, 1992, now abandoned.

SUMMARY OF THE INVENTION

The present invention relates to a pharmaceutical composition and method for the treatment of circulatory disorders, comprising a tetrahydronaphthalene derivative of the formula

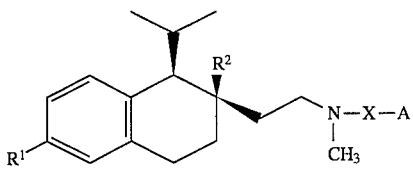

I wherein $R^1$ is halogen, $R^2$ is lower-alkoxy-lower-alkyl-carbonyloxy, X is $C_2$–$C_8$-alkylene and A is benzimidazolyl optionally substituted at the N atom by alkyl with 1 to 12 C atoms,
and a pyridazodiazepine of the formula

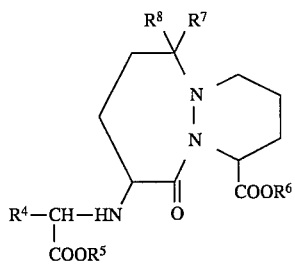

II wherein $R^4$ is aralkyl, $R^5$ and $R^6$ each independently are hydrogen or alkyl with 1 to 6 C atoms and $R^7$ and $R^8$ each are hydrogen or together are an oxo group,
whereby the active substances can be present either in the form of their free bases, their hydrates or their pharmaceutically usable salts.

DETAILED DESCRIPTION

Figure 1:
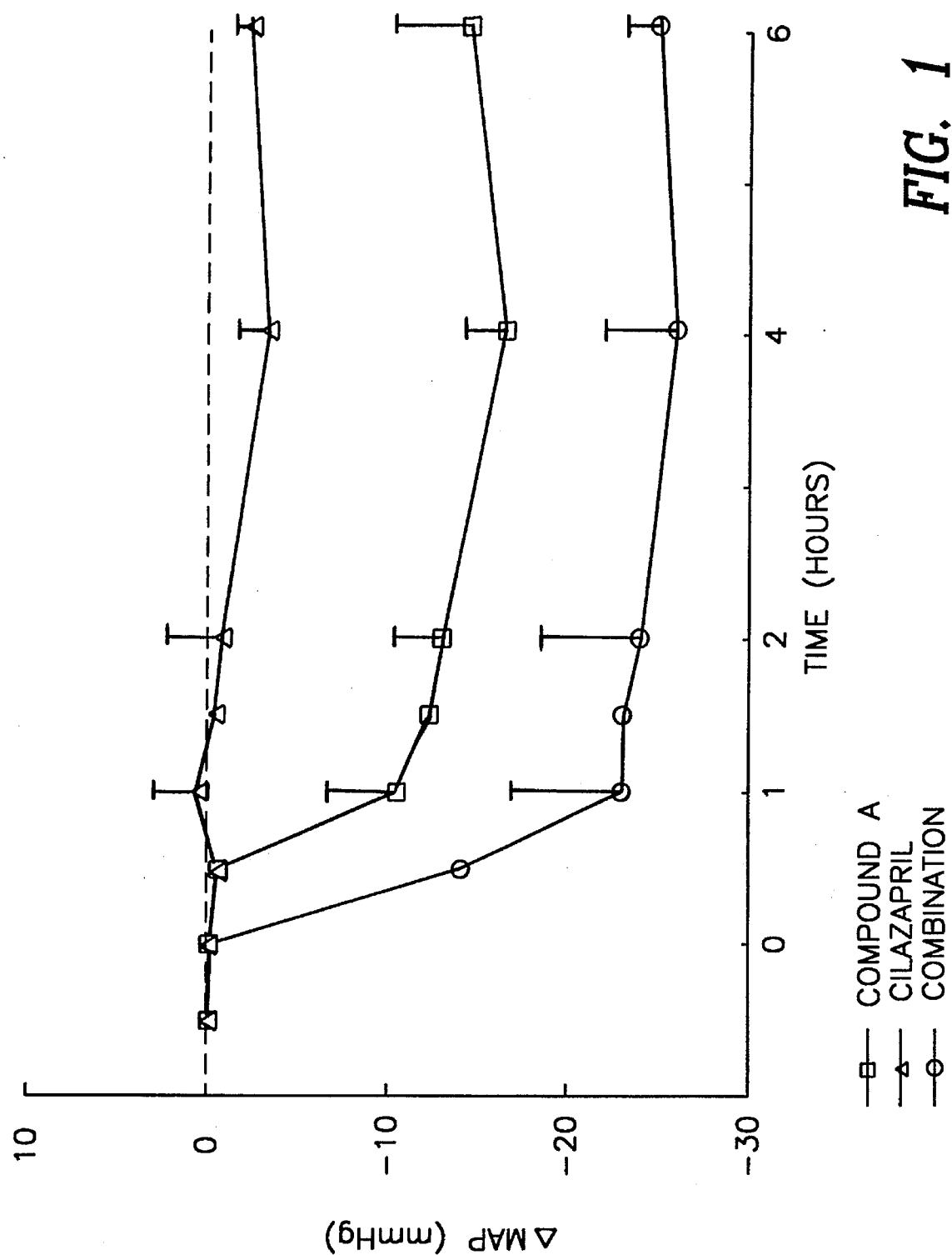
FIGS. 1 and 2 are plots illustrating the effect of cilazapril and compound A, alone and in combination, on blood pressure over time.

The tetrahydronaphthalene derivatives of the invention are calcium antagonists disclosed in EP-A 0,268,148 and are suitable for the treatment of hypertension, see, for example, Clozel et al., Cardiovasc. Drug Rev. 9, 4–17 (1991).

The pyridazodiazepines of the invention are known angiotensin convening enzyme (ACE) inhibitors and are, accordingly, useful for the treatment of hypertension as described in EP-A 0,094,095.

The treatment of hypertension by the simultaneous administration of the blood pressure-lowering calcium antagonist nitrendipine and the ACE inhibitor captopril has shown that the patients treated with nitrendipine and captopril with the simultaneous administration of the two active substances have a better overall response than with the sole administration of captopril or nitrendipine. [J. Cardiovasc. Pharmacol. 7, S88–S91 (1985)]. In these trials, both of the individual components were used in the dosages conventional for the respective monotherapy.

However, there still exists the need to provide a pharmaceutical combination, the administration of which leads to a lowering of the blood pressure, in which the dosages of the individual components are significantly reduced and undesired side effects, which appear in each case using the necessary dosages in monotherapy, can be suppressed.

In the scope of the present invention, it has been established that with the administration of the combination in accordance with the invention of a tetrahydronaphthalene derivative with a pyridazodiazepine the blood pressure lowering-properties of the individual components are not only additive, but are surprisingly potentiated, whereby the effective dosages of the two individual components can be decreased significantly.

The antihypertensive combination in accordance with the invention accordingly has the following advantages:

a) the amounts of active ingredients to be administered are reduced significantly;

b) undesired side effects are eliminated or greatly reduced;

c) both individual components have a similar long biological half life of 10–12 hours in the treatment of hypertension in human beings. The course of the effect is therefore expected to be equivalent;

d) both individual components have a high bioavailability, for example, 80–100% for the most preferred tetrahydronaphthalene derivative, that is [1S,2S]-2-[2-[[3-(2-benzimidazolyl)propyl]methylamino]ethyl]-6-fluoro-1,2,3,4-tetrahydro-1-isopropyl-2-naphthylmethoxyacetate dihydrochloride (referred to as Compound A hereinafter) and, for example, 70% for the most preferred pyridazodiazepine, that is, 9(S)-[1(S)-ethoxycarbonyl-3-phenylpropylamino]octahydro-10-oxo-6H-pyridazo[1,2-a][1,2]diazepine-1(S)-carboxylic acid (referred to as cilazapril hereinafter).

The invention relates to a pharmaceutical composition and method for the simultaneous, separate or planned stepwise use in the treatment of hypertension, comprising a tetrahydronaphthalene derivative of the formula:

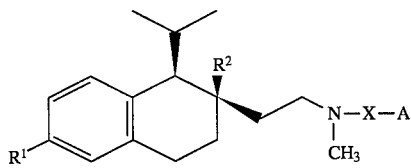

I wherein $R^1$ is halogen, $R^2$ is lower-alkoxy-lower-alkyl-carbonyloxy, X is $C_2$–$C_8$-alkylene and A is benzimidazolyl optionally substituted at the N atom by alkyl with 1 to 12 C atoms,
and a pyridazodiazepine of the formula

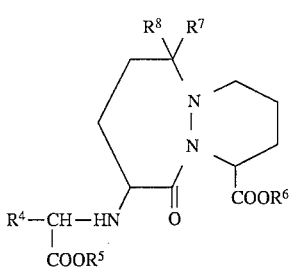

wherein $R^4$ is aralkyl, $R^5$ and $R^6$ each independently are hydrogen or alkyl with 1 to 6 C atoms and $R^7$ and $R^8$ each are hydrogen or together are an oxo group, whereby the active substances can be present either in the form of their free bases, their hydrates or their pharmaceutically usable salts.

The aryl residue in aralkyl is a phenyl group which can be mono-substituted by halogen, for example, fluorine, chlorine, bromine or iodine; alkoxy with 1 to 6 C atoms; or phenyl. The alkyl residue in aralkyl has 1 to 6 C atoms. Benzyl, 2-phenylethyl, 3-phenylpropyl, 2-(4-chlorophenyl)ethyl, 2-(4-methoxyphenyl)ethyl and the like are examples of aralkyl groups.

The weight ratio of tetrahydronaphthalene derivative to pyridazodiazepine is conveniently 100:1 to 1:1, preferably 20:1 to 2:1.

Advantageously, the dosage of a combination to be administered per day is 5 to 100 mg of a tetrahydronaphthalene derivative and 1 to 5 mg of a pyridazodiazepine. In general, the total amount of a tetrahydronaphthalene derivative and a pyridazodiazepine derivative to be administered daily is a maximum of 55 mg. When a hydrate or a pharmaceutically usable salt is used, then the above values have to be altered appropriately.

Objects of the invention are
a combination of a tetrahydronaphthalene derivative and a pyridazodiazepine;

a pharmaceutical preparation comprising a tetrahydronaphthalene derivative and a pyridazodiazepine; and the use of a combination of a tetrahydronaphthalene derivative and a pyridazodiazepine and, respectively, of a pharmaceutical preparation containing a tetrahydronaphthalene derivative and a pyridazodiazepine for the control or prevention of illnesses, especially of circulatory disorders, particularly in the control or prevention of hypertension and disorders stemming therefrom.

Particularly preferred compounds of formula I are:
2-[2-[[3-(2-Benzimidazolyl)propyl]methylamino]ethyl]-6-fluoro-1,2,3,4-tetrahydro-1α-isopropyl-2α-naphthyl-methoxyacetate as well as Compound A.

Especially suitable pyridazodiazepines are those of formula II in which $R^4$ is aralkyl, $R^5$ is alkyl with 1 to 4 C atoms, $R^6$ is hydrogen and $R^7$ and $R^8$ each are hydrogen or together are an oxo group.

Particularly suitable pyridazodiazepines are those of formula II in which $R^4$ is phenyl-$C_{1-4}$-alkyl, $R^5$ is alkyl with 1 to 4 carbon atoms and $R^6$, $R^7$ and $R^8$ each are hydrogen.

Cilazapril is the most suitable representative from the group of pyridazodiazepines of formula II.

A regular and long-lasting blood pressure-lowering effect can be achieved with the combination in accordance with the invention using low dosages of active substances.

The advantageous more than additive blood pressure-lowering effect of the combination in accordance with the invention vis-à-vis that of the two individual components will be evident having regard to the test described hereinafter.

The antihypertensive effect of the combination was investigated in conscious dogs having renal hypertension. The hypertension was produced in German sheepdogs (weight 23–30 kg) using known methods in which one kidney is wrapped with cellophane and a stenosis is formed in the renal artery of the contralateral kidney using an occluder. The blood pressure was measured with a catheter implanted in the abdominal aorta and connected to a transmitter in the abdominal, cavity (telemetry).

FIG. 1 illustrates the effect of cilazapril (10 mg/kg per os) and Compound A (30 mg/kg per os) alone, as well as, the effect of the simultaneous administration of the same dosages of the two substances (n=3 dogs for cilazapril and the combination, n=4 dogs for Compound A). Cilazapril alone was without effect and Compound A lowered the blood pressure (MAP) by 10–20 mmHg. The combination was substantially more active at all points in time.

Figure 2:
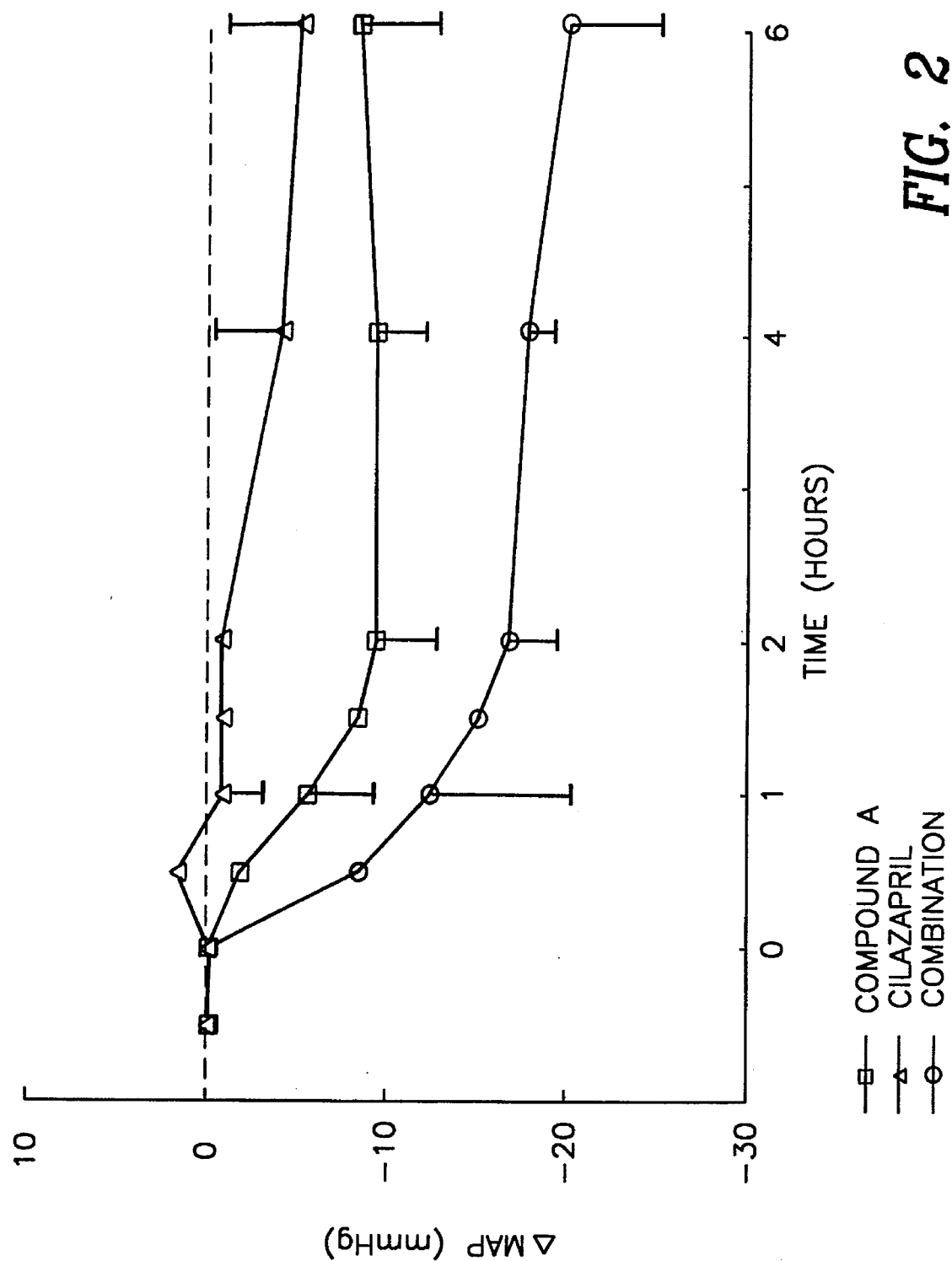

The synergistic effect of the combination was also evident in a further series of experiments in which the dosages of the components were lower, namely 3 mg/kg per os for cilazapril and 10 mg/kg per os for Compound A (same number of test animals). The result obtained in this series of experiments is shown in FIG. 2.

The advantageous more than additive effect of the combination in accordance with the invention vis-à-vis that of the two individual components in the known regression of the chronic hypertension-caused hypertrophy of the media in the large, muscular arteries by treatment of the hypertension with ACE inhibitors and other customary therapeutics [Hypertension 9, 178–187 (1987)] can be demonstrated with the aid of the test described hereinafter.

The influence of the individual compounds and their combination on the blood vessels was investigated in rats. Male rats, strain: RoRo (weight about 400 g; aged 4–5 months; Institut für Biologisch-Medizinische Forschung, F üllinsdorf, CH) were used. The animals were divided randomly into a control group and into treatment groups. The duration of the treatment was 15 days. Cilazapril was admixed with the feed in an amount such that the daily intake was on average 10 mg/kg and Compound A (30 mg/kg) was administered using a probang. The control animals received the same laboratory feed without additive.

After 15 days, the rats were anaesthetized with ether and the carotid artery was fixed by perfusion with fixative agent (2.5% glutaraldehyde in 0.1M phosphate buffer, pH 7.4). For this, a probe was passed through the left ventricle of the heart into the ascending aorta (inflow) and a second probe was pushed through the right ventricle into the auricle (discharge). The vascular system was firstly rinsed with 10 ml of buffered isotonic NaCl solution and then fixed for 15 minutes with fixative at a pressure of 11.7 kPa. Subsequently, the right carotid artery was dissected, freed from adhering tissue and placed in 2.5% glutaraldehyde for further fixation. Each artery was divided into five vascular segments from the distal end to the proximal end, dehydrated and embedded in EPON 12 (Registered Mark of Shell A.G.). The middle segment was used for the morphological investigations. Semi-thin cross-sections (1 μm thick) were colored with toluidine blue and basic fuchsin. The cross-section surface of the media was measured with the morphometry system DIASYS (Datalab, Heinz Meyer, CH-3367 Thörigen).

Figure 3:
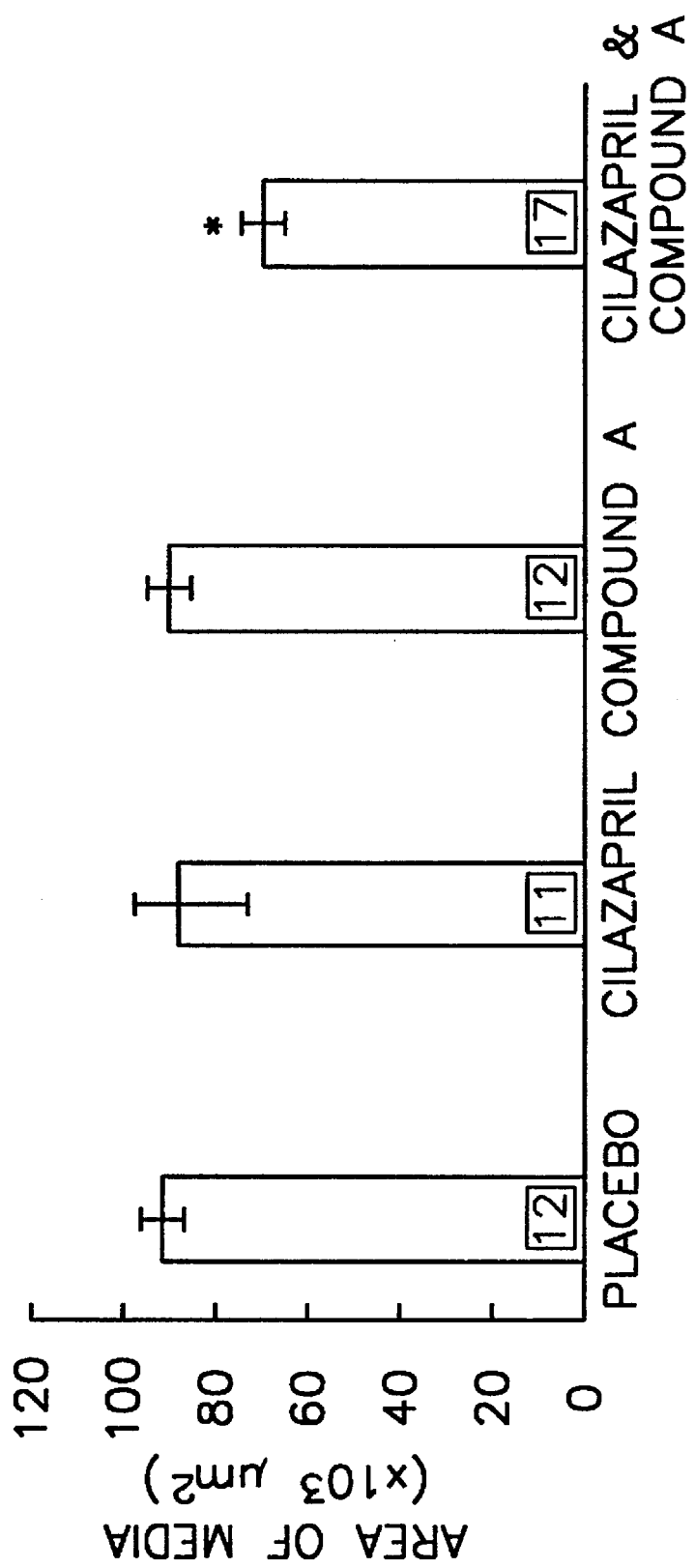
FIG. 3 is a bar graph illustrating the effect of cilazapril and compound A, alone and in combination, on the area of the media.

The area of the media in the control animals was 89000±5000 μm². The individual treatment was without effect (84000±11000 μm² in the case of cilazapril and 87000±4000 μm² in the case of Compound A). See also FIG. 3, the numbers in the columns relate to the number of experimental animals in the respective groups. The combination lowers the media area by 15% to 74000±4000 μm² (statistically significant; p<0.05 with the t-test according to Student).

The decrease in the media surface by the combination was confirmed in a second series of experiments.

A mechanistic interaction apparently exists between ACE inhibitors and calcium antagonists. It is known that by the administration of a calcium antagonist and the lowering of the blood pressure resulting therefrom, a compensatory stimulation of the renin angiotensin system is effected. This compensation is suppressed by the use of the ACE inhibitor.

The foregoing results show the unexpected advantageous properties of the combinations in accordance with the invention. With a knowledge of the state of the art, it could not be expected that just the combination of tetrahydronaphthalene derivatives, especially of Compound A, with pyridazodiazepines, especially with cilazapril, would show such an optimal blood pressure-lowering activity.

The combinations in accordance with the invention are generally administered orally, for example, in the form of tablets, varnished tablets, dragées, hard and soft gelatin capsules, solutions, emulsions or suspensions. The administration can, however, also be effected rectally, for example, in the form of suppositories, or parenterally, for example, in the form of injectable solutions.

A combination in accordance with the invention can be processed with pharmaceutically inert, inorganic or organic excipients for the preparation of tablets, varnished tablets, dragées and hard gelatin capsules. Lactose, corn starch or derivatives thereof, talc, stearic acid or its salts and the like can be used, for example, as such excipients for tablets, dragées and hard gelatin capsules.

Suitable excipients for soft gelatin capsules are, for example, vegetable oils, waxes, fats, semi-solid and liquid polyols and the like; depending on the nature of the active substance, no excipients are generally required in the case of soft gelatin capsules.

Suitable excipients for the preparation of solutions and syrups are, for example, water, polyols, saccharose, invert sugar, glucose and the like.

Suitable excipients for injectable solutions are, for example, water, alcohols, polyols, glycerol, vegetable oils and the like.

Suitable excipients for suppositories are, for example, natural or hardened oils, waxes, fats, semi-liquid or liquid polyols and the like.

Moreover, the pharmaceutical preparations can contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances.

The following Examples illustrate the invention.

EXAMPLE 1

Production of varnished tablets of the following composition:

Tablet cores:

| | | |
|---|---|---|
| a. | Compound A | 29.07 mg (= 25 mg of base) |
| b. | Cilazapril | 1.25 mg |
| c. | Lactose anhydrous | 70.18 mg |
| d. | Corn starch white | 30.00 mg |
| e. | Polyvinylpyrrolidone | 5.00 mg |
| f. | Talc | 5.00 mg |
| g. | Sodium stearyl fumarate | 1.50 mg |
| Weight per tablet core | | 142.00 mg |

Varnish coating:

| | | |
|---|---|---|
| h. | Hydroxypropylmethylcellulose | 4.00 mg |
| i. | Polyethylene glycol 6000 | 1.00 mg |
| j. | Titanium dioxide | 1.60 mg |
| k. | Talc | 1.40 mg |
| Varnish coating weight | | 8.00 mg |
| Total weight per varnished tablet | | 150.00 mg |

Production Procedure:

Production of the Tablet Core:

b is homogeneously mixed successively and portionwise with c and sieved. Then, a, d and e are added and the mixture is mixed briefly, sieved and moistened for a suitable period in a planetary mixer. The moist mass is granulated through a suitable sieve, dried and subsequently broken up in a suitable sieve. Thereto there are added the sieved f and g and the mixture is mixed homogeneously. The ready-to-press mixture is pressed to tablet cores of suitable size and form (with or without a breakbar) weighing 142.0 mg.

Production of the Varnish Coating:

An aqueous varnishing suspension is prepared from h to k and the tablet cores are coated with this in a suitable manner with the aid of a varnishing process in a coating kettle or another varnishing apparatus until the varnished tablets have achieved a final weight of 150 mg.

EXAMPLE 2

Production of Hard Gelatin Capsules of the Following Composition:

| | | |
|---|---|---|
| a. | Compound A | 29.07 mg (= 25 mg of base) |
| b. | Cilazapril | 2.50 mg |
| c. | Lactose powd. | 26.93 mg |
| d. | Lactose cryst. | 60.00 mg |
| e. | Microcrystalline cellulose | 50.00 mg |
| f. | Talc | 10.00 mg |
| g | Sodium stearyl fumarate | 1.50 mg |
| Fill weight per capsule | | 180.00 mg |

Production Procedure:

b is homogeneously mixed successively and portionwise with c, sieved and the sieved a, d and e are added and mixed in a suitable manner. The sieved f and g are added thereto and mixed for a suitable period. The ready-to-fill final mixture is filled into hard gelatin capsules of suitable size and color.

EXAMPLE 3

Production of Varnished Tablets CR (Controlled Release) of the Following Composition:

CR tablet core:

| | | |
|---|---|---|
| a. | Compound A | 58.13 mg (= 50 mg of base) |
| b. | Cilazapril | 2.50 mg |
| c. | Lactose anhydrous | 45.37 mg |
| d. | Methocel (Registered Mark of Dow Chemical Company) | 10.00 mg |
| e. | Hydroxypropylcellulose | 10.00 mg |
| f. | Talc | 4.00 mg |
| g. | Sodium stearyl fumarate | 2.00 mg |
| Weight per CR tablet core | | 132.00 mg |

-continued

| Varnish coating: | |
|---|---|
| h. Hydroxypropyl-methylcellulose | 4.00 mg |
| i. Polyethylene glycol 6000 | 1.00 mg |
| j. Titanium dioxide | 1.60 mg |
| k. Talc | 1.40 mg |
| Varnish coating weight | 8.00 mg |
| Total weight per CR varnished tablet | 140.00 mg |

Production Procedure
Production of the CR Tablet Core:

b is homogeneously mixed successively and portionwise with c and sieved, and the sieved a, d and e are subsequently admixed and compacted on a rolling compactor in a suitable manner. The compacted material is sieved through a suitable sieve and subsequently mixed homogeneously with a sieved mixture of f and g and pressed to tablet cores of 132.0 mg in suitable size and form.

Production of the Varnish Coating:

An aqueous varnish suspension is produced from h to k and the tablet cores are coated with this in a suitable manner with the aid of a varnishing process in a coating kettle or another varnishing apparatus until the vanished tablets have achieved a final weight of 140 mg.

EXAMPLE 4

Production of CR Pellet Formulations of the Following Composition In Hard Gelatin Capsules:

| Pellets: | |
|---|---|
| a. Compound A | 58.13 mg (= 50 mg of base) |
| b. Cilazapril | 2.50 mg |
| c. Microcrystalline cellulose | 139.37 mg |
| Weight of pellet core per capsule | 200.00 mg |
| CR pellet varnish: | |
| d. Ethylcellulose (AQUACOAT dispers.) | 16.00 mg |
| e. Dibutyl sebacate | 4.00 mg |
| Wt. varnished pellet core/capsule | 20.00 mg |
| Total weight CR pellets per capsule | 220.00 mg |

Production Procedure:
Production of the Pellet Cores:

a, b and c are homogeneously mixed with one another in a suitable manner, moistened with the appropriate amount of water in a mixer and extruded through a suitable perforated disk. The extruded mass is broken up in a spheronizer, rounded-off and subsequently dried in a fluidized bed.

Production of the Varnish Coating:

The pellet cores are coated with the aqueous dispersion of d and e in a continuous process using a fluidized bed spray procedure under suitable conditions until the varnish coating amounts to 10% of the weight of the pellet cores. Subsequently, the varnished CR pellets are subjected to a heat treatment and filled to 220 mg into hard gelatin capsules of suitable size and color.

We claim:

1. A pharmaceutical composition comprising [1S,2S]-2-[2-[[3-(2-benzimidazolyl)propyl]methylamino]ethyl]-6-fluoro-1,2,3,4-tetrahydro-1-isopropyl-2-naphthylmethoxyacetate dihydrochloride and 9(S)-[1(S)-ethoxycarbonyl-3-phenylpropylamino]octahydro-10-oxo-6H-pyridazo[1,2-a][1,2]diazepine-1-(S)-carboxylic acid hydrate wherein the weight ratio of [1S,2S]-2-[2-[[3-(2-benzimidazolyl)propyl]methylamino]ethyl-6-fluoro-1,2,3,4-tetrahydro-1-isopropyl-2-naphthylmethoxyacetate dihydrochloride to 9(S)-[1-(S)-ethoxycarbonyl-3-phenylpropyl-amino]octahydro-10-oxo-6H-pyridazo[1,2-a][1,2]diazepine-1-(S)-carboxylic acid hydrate is about 3:1.

2. A method for the control of hypertension and disorders induced by hypertension comprising administering to a host in need of such treatment an effective amount of a combination of [1S,2S]-2-[2-[[3-(2-benzimidazolyl)propyl]methylamino]ethyl]-6-fluoro-1,2,3,4-tetrahydro-1-isopropyl-2-naphthylmethoxyacetate dihydrochloride and 9(S)-[1(S)-ethoxycarbonyl-3-phenylpropylamino]octahydro-10-oxo-6H-pyridazo[1,2-a][1,2]diazepine-1(S)-carboxylic acid hydrate wherein the weight ratio of [1S,2S]-2-[[3-(2-benzimidazolyl)propyl]methylamino]ethyl-6-fluoro-1,2,3,4-tetrahydro-1-isopropyl-2-naphthylmethoxyacetate dihydrochloride to 9(S)-[1-(S)-ethoxycarbonyl-3-phenylpropylamino]octahydro-10-oxo-6H-pyridazo[1,2-a][1,2]diazepine-1-(S)-carboxylic acid hydrate is about 3:1.

* * * * *